US012582488B2

(12) United States Patent
Wang et al.

(10) Patent No.: US 12,582,488 B2
(45) Date of Patent: Mar. 24, 2026

(54) USER INTERFACE FOR CONNECTING MODEL STRUCTURES AND ASSOCIATED SYSTEMS AND METHODS

(71) Applicant: Intuitive Surgical Operations, Inc., Sunnyvale, CA (US)

(72) Inventors: Bai Wang, Palo Alto, CA (US); Shiyang Chen, Sunnyvale, CA (US); Joy Janku, San Francisco, CA (US); Sida Li, San Jose, CA (US); Hui Zhang, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 182 days.

(21) Appl. No.: 18/552,137

(22) PCT Filed: Apr. 5, 2022

(86) PCT No.: PCT/US2022/023490
§ 371 (c)(1),
(2) Date: Sep. 22, 2023

(87) PCT Pub. No.: WO2022/216716
PCT Pub. Date: Oct. 13, 2022

(65) Prior Publication Data
US 2024/0164853 A1     May 23, 2024

Related U.S. Application Data

(60) Provisional application No. 63/171,996, filed on Apr. 7, 2021.

(51) Int. Cl.
*G06T 19/00* (2011.01)
*A61B 34/00* (2016.01)
(Continued)

(52) U.S. Cl.
CPC .............. *A61B 34/25* (2016.02); *A61B 34/35* (2016.02); *G06T 19/00* (2013.01); *A61B 2034/105* (2016.02); *A61B 2034/107* (2016.02); *A61B 2034/2051* (2016.02); *A61B 2034/2061* (2016.02); *A61B 2034/303* (2016.02); *G06T 2200/24* (2013.01); *G06T 2210/41* (2013.01)

(58) Field of Classification Search
None
See application file for complete search history.

(56) References Cited

U.S. PATENT DOCUMENTS 6,380,732 B1     4/2002 Gilboa
6,389,187 B1     5/2002 Greenaway et al.
(Continued)

FOREIGN PATENT DOCUMENTS

WO     WO-2018106950 A1     6/2018
WO     WO-2020186015 A1     9/2020

OTHER PUBLICATIONS

Graham M.W., et al., "Robust 3-D Airway Tree Segmentation for Image-guided Peripheral Bronchoscopy," IEEE Transactions on Medical Imaging, Apr. 2010, vol. 29 (4), pp. 982-997.
(Continued)

*Primary Examiner* — Saptarshi Mazumder
(74) *Attorney, Agent, or Firm* — Haynes & Boone, LLP.

(57) ABSTRACT

Devices, systems, methods, and computer program products for performing medical procedures are disclosed herein. In some embodiments, a system for planning a medical procedure is configured to receive a three-dimensional (3D) model of an anatomic region of a patient. The 3D model can include a set of linked structures and at least one isolated structure spaced apart from the linked structure. The system can output a graphical representation of the linked structures and the at least one isolated structure, and can receive
(Continued)

operator input indicating a set of locations on the graphical representation. The set of locations can represent a connection between the at least one isolated structure and the linked structures. Based on the operator input, the system can generate a bridge structure connecting the at least one isolated structure to the linked structures.

20 Claims, 10 Drawing Sheets

(51) Int. Cl.
| | |
|---|---|
| *A61B 34/35* | (2016.01) |
| *A61B 34/10* | (2016.01) |
| *A61B 34/20* | (2016.01) |
| *A61B 34/30* | (2016.01) |

(56) References Cited

U.S. PATENT DOCUMENTS

| | | | |
|---|---|---|---|
| 7,316,681 B2 | 1/2008 | Madhani et al. | |
| 7,772,541 B2 | 8/2010 | Froggatt et al. | |
| 7,781,724 B2 | 8/2010 | Childers et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 9,672,631 B2 * | 6/2017 | Higgins | G06T 7/162 |
| 11,871,904 B2 * | 1/2024 | Inglis | A61B 1/0005 |
| 2018/0189953 A1 * | 7/2018 | Nie | G06T 7/174 |
| 2020/0060771 A1 * | 2/2020 | Lo | A61B 34/20 |

OTHER PUBLICATIONS

International Search Report and Written Opinion for Application No. PCT/US2022/023490 mailed Jul. 27, 2022, 13 pages.

Medslicer: "Organ segmentation 3.2: Lungs vessels," Aug. 5, 2019, Retrieved from the Internet: URL: https://www.youtube.com/watch?v=wS6-4dwZCfo , 17 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Preliminary Report on Patentability for Application No. PCT/US2022/023490, mailed Oct. 19, 2023, 11 pages.

* cited by examiner

USER INTERFACE FOR CONNECTING MODEL STRUCTURES AND ASSOCIATED SYSTEMS AND METHODS

CROSS-REFERENCE APPLICATIONS

This patent application is the U.S. National Stage patent application of International Patent Application No. PCT/US2022/023490 filed on Apr. 5, 2022 which claims priority to and the benefit of U.S. Provisional Application No. 63/171,996, filed Apr. 7, 2021 and entitled "USER INTERFACE FOR CONNECTING MODEL STRUCTURES AND ASSOCIATED SYSTEMS AND METHODS," each of which is incorporated by reference herein in its entirety.

TECHNICAL FIELD

The present disclosure is directed to systems, methods, and computer program products for connecting structures in an anatomic model for a medical procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy. Navigation may be assisted using images of the anatomic passageways. Improved systems and methods are needed to accurately model the anatomic passageways.

SUMMARY

Disclosed herein are devices, systems, methods, and computer program products for planning a medical procedure. In some embodiments, a system for planning a medical procedure includes a processor and a memory operably coupled to the processor. The memory can store instructions that, when executed by the processor, cause the system to perform operations including receiving a three-dimensional (3D) model of an anatomic region of a patient. The 3D model can include a set of linked structures and at least one isolated structure spaced apart from the linked structure. The operations can also include outputting a graphical representation of the linked structures and the at least one isolated structure, and receiving operator input indicating a set of locations on the graphical representation. The set of locations can represent a connection between the at least one isolated structure and the linked structures. The operations can further include generating, based on the operator input, a bridge structure connecting the at least one isolated structure to the linked structures.

In these and other embodiments, a non-transitory, computer-readable medium can store instructions thereon that, when executed by one or more processors of a computing system, cause the computing system to perform operations including outputting a graphical user interface. The graphical user interface can include a 3D model of an anatomic region of a patient, the 3D model including a set of linked structures and at least one isolated structure spaced apart from the linked structures. The graphical user interface can also include a plurality of two-dimensional (2D) images of the anatomic region of the patient. The operations can also include receiving, via the graphical user interface, operator input indicating a set of locations in one or more of the 3D model or the 2D images, the set of locations representing a connection between the at least one isolated structure and the linked structures. The operations can further include updating the 3D model, based on the operator input, to include a bridge structure connecting the at least one isolated structure to the linked structures.

In these and still other embodiments, a method can include receiving a 3D anatomic model including a set of linked structures and at least one isolated structure disconnected from the linked structures. The method can also include outputting a graphical user interface displaying the linked structures and the at least one isolated structure. The method can further include receiving, via the graphical user interface, operator input defining a connection between the at least one isolated structure and the linked structures. The method can include generating, based on the operator input, a bridge structure connecting the at least one isolated structure to the linked structures.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

Figure 1:
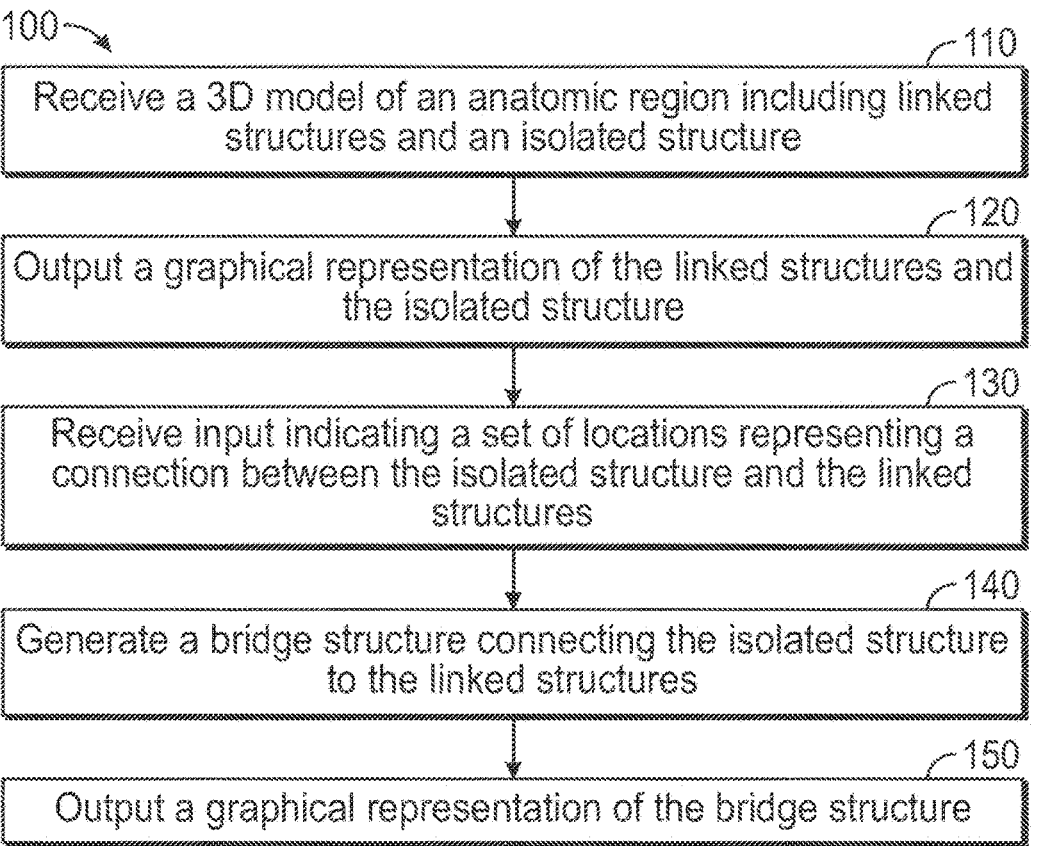
FIG. 1 is a flow diagram illustrating a method for planning a medical procedure in accordance with various embodiments of the present technology

The present disclosure is directed to devices, systems, methods, and computer program products for planning a medical procedure. In some embodiments, an image-guided medical procedure uses a 3D model of an anatomic region to assist an operator in visualizing the patient anatomy and/or navigating a medical device within the anatomic region. The 3D model can be generated from images of the anatomic region (e.g., computed tomography (CT) image data and/or other types of 3D volume image data including a stack or series of 2D image slices) using an image segmentation algorithm and/or other image processing techniques. In some situations, however, the generated model can include structures or portions that are not connected to the rest of the model (referred to herein as "isolated structures"). Isolated structures may result, for example, from incomplete image data, poor image quality, previous surgical or radiation intervention, mucus or other blockages, and/or issues with the segmentation algorithm. The presence of isolated structures may interfere with planning a medical procedure in the anatomic region, particularly if the isolated structures are close to a target site for the procedure (e.g., a biopsy site). However, conventional user interfaces for planning a medical procedure may simply discard or hide the isolated structures in the 3D model, such that the operator is unaware of the isolated structures and/or cannot control how the isolated structures are rejoined to the rest of the model.

The present technology can address these and other challenges by providing graphical user interfaces that allow the operator to view the isolated structures and provide input indicating how the isolated structures should be connected to the other structures in the 3D model (referred to herein as "linked structures"). In some embodiments, for example, the systems disclosed herein are configured to receive a 3D model of an anatomic region (e.g., the airways of the lungs). The 3D model can include a set of linked structures (e.g., connected airways) and at least one isolated structure (e.g., a disconnected portion of the airways). The system can output a graphical representation of the linked structures and the isolated structure, such as a graphical user interface showing the 3D model and/or at least some of the 2D images used to generate the 3D model. The operator can provide input indicating a set of locations in the graphical representation that represent a connection between the isolated structure and the linked structures. Based on the operator input, the system can generate a bridge structure connecting the isolated structure to the linked structure, such as by "growing" the bridge structure from the selected locations using a suitable segmentation algorithm.

In some embodiments, the present technology is expected to provide a fast and easy way for the operator to reconnect isolated structures, thus improving the accuracy and flexibility of the modeling process. Operator input can also be helpful for ensuring that the isolated structures are actually part of the patient anatomy, rather than being imaging artifacts or non-anatomic structures (e.g., mucus or debris). Additionally, the present technology is expected to assist the operator in verifying that the generated connection is anatomically accurate by providing a graphical user interface that displays both the 3D model and the 2D images used to produce the model.

A. EMBODIMENTS OF PROCESSES AND USER INTERFACES FOR CONNECTING MODEL STRUCTURES

FIG. 1 is a flow diagram illustrating a method 100 for planning a medical procedure in accordance with various embodiments of the present technology. The method 100 is illustrated as a set of steps or processes 110-150. All or a subset of the steps of the method 100 can by implemented by any suitable computing system or device, such as a control system of a medical instrument system or device (e.g., including various components or devices of a robotic or teleoperated system), a workstation, a portable computing system (e.g., a laptop computer), and/or a combination thereof. In some embodiments, the computing system for implementing the method 100 includes one or more processors operably coupled to a memory storing instructions that, when executed, cause the computing system to perform operations in accordance with the steps 110-150. The method 100 is illustrated in the following description by cross-referencing various aspects of FIGS. 2-5.

The method 100 begins at step 110 with receiving a 3D model of an anatomic region of a patient. The model can represent an anatomic region in which a medical procedure is to be performed, and can depict the locations, shapes, and connectivity of the passageways and/or other anatomic structures within that region. The model can also depict one or more target sites within the anatomic region that will be accessed, biopsied, treated, etc., during the medical procedure. In some embodiments, for example, the anatomic region is or includes the airways of the patient's lungs, and the target site can be a biopsy target within the lungs such as a lesion or nodule. Accordingly, an operator can use the model to plan the medical procedure, such as by determining a path for a medical instrument or device to navigate through the passageways to reach the target site(s).

The 3D model can be generated in a number of different ways. In some embodiments, for example, the 3D model is generated from preoperative and/or intraoperative image data of the anatomic region, such as CT data, cone beam CT (CBCT) data, tomosynthesis data, magnetic resonance imaging (MRI) data, fluoroscopy data, thermography data, ultrasound data, optical coherence tomography (OCT) data, thermal image data, impedance data, laser image data, nanotube X-ray image data, and/or other suitable data representing the patient anatomy. The image data can correspond to 2D, 3D, or four-dimensional (e.g., time-based or velocity-based information) images. In some embodiments, for example, the image data includes 2D images from multiple perspectives that can be combined into pseudo-3D images.

The 3D model can be generated by segmenting graphical elements in the image data that represent anatomic features or structures. During the segmentation process, graphical units (e.g., pixels or voxels) generated from the image data may be partitioned into segments or elements and/or be tagged to indicate that they share certain characteristics or computed properties such as color, density, intensity, and/or texture. The segments or elements associated with anatomic features of the patient are then converted into a segmented anatomic model, which is generated in a model or image reference frame. To represent the model, the segmentation process may delineate sets of voxels representing the anatomic region and then apply a function, such as a marching cube function, to generate a 3D surface that encloses the voxels. The model may be made by generating a mesh, volume, or voxel map. Additionally or alternatively, the model may include a centerline model that includes a set of interconnected line segments or points extending through the centers of the modeled passageways. In instances where the model includes a centerline model including a set of interconnected line segments, those line segments may be converted to a cloud or set of points. By converting the line segments, a desired quantity of points corresponding to the interconnected line segments can be selected manually or automatically.

The segmented 3D model can include a plurality of linked structures or segments representing passageways within the anatomic region, such that the connections between the linked structures correlate to the connections between the passageways in the actual anatomy. However, the 3D model may also include one or more isolated structures or segments that are disconnected from the rest of the model (e.g., the isolated structures do not contact and/or overlap the linked structures). The isolated structures may represent anatomic passageways that are connected to other passageways in the actual anatomy, but are erroneously depicted as discontinuous components in the 3D model. Such isolated structures can arise for various reasons, such as insufficient image quality, incomplete image data, blockages in the anatomy, and/or issues with the segmentation algorithm (e.g., the algorithm fails to segment certain passageways from the image data). However, some of the isolated structures may correspond to non-anatomic structures in the patient's body (e.g., mucus or debris), or may be imaging or modeling artifacts that are not actually present in the anatomy.

Figure 2:
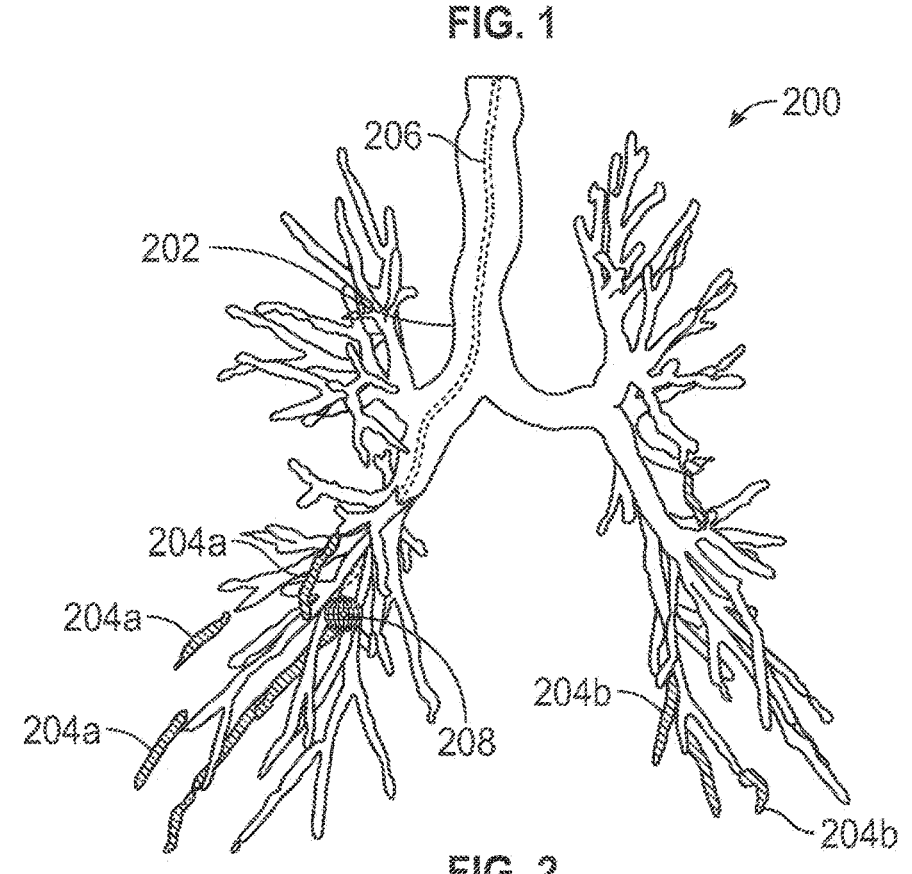
FIG. 2 illustrates a representative example of a 3D model configured in accordance with embodiments of the present technology.

FIG. 2 illustrates a representative example of a 3D model 200 configured in accordance with embodiments of the present technology. In the illustrated embodiment, the 3D model 200 depicts the airways of the lungs, and includes a plurality of linked structures 202 representing the branched passageways within the lungs (e.g., main carina, left main bronchus, right main bronchus, secondary bronchi, tertiary bronchi, etc.). In other embodiments, however, the 3D model 200 can represent other anatomic regions that may or may not include branched passageways. The 3D model 200 can include one or more isolated structures (indicated by hatching) that are disconnected from the linked structures 202, such as one or more first isolated structures 204a on a first (e.g., right) side of the lungs, and one or more second isolated structures 204b on a second (e.g., left) side of the lungs. As discussed above, some or all of the isolated structures 204a-b can represent passageways that should be reconnected to the linked structures 202 in order to accurately represent the connectivity in the actual patient anatomy. Optionally, some of the isolated structures 204a-b can correspond to mucus, debris, or artifacts, and therefore should not be reconnected to the linked structures 202. In some embodiments, it may be difficult to accurately differentiate the isolated structures 204a-b that represent actual anatomy from the isolated structures 204a-b that represent non-anatomic structures and/or artifacts, without operator review and/or intervention.

The 3D model 200 can be used by the operator to plan a path 206 (e.g., for a medical device) to reach a target site 208. In the illustrated embodiment, some of the first isolated structures 204a are located near the target site 208, and may therefore make it difficult or impossible to plan an optimal path 206 to the target site 208. To avoid such issues, some or all of the first isolated structures 204a can be reconnected to the linked structures 202, as described in detail below. In some embodiments, because the second isolated structures 204b are located relatively far from the target site 208, the second isolated structures 204b may not need to be reconnected to the linked structures 202. In other embodiments, however, some or all of the second isolated structures 204b can also be reconnected, in accordance with the techniques described further herein.

Referring again to FIG. 1, step 110 can optionally include analyzing the 3D model to identify the presence and/or locations of any isolated structures, e.g., in an automatic manner, based on operator input, or suitable combinations thereof. For example, the spatial relationship of the various structures in the 3D model can be analyzed to automatically detect any structures that are not connected to the rest of the model. In some embodiments, the largest set or volume of continuous components in the model are automatically designated to be the linked structures, and any model components that are not connected to those continuous components are identified as isolated structures. Alternatively or in combination, the model components representing a specified portion of the anatomy (e.g., the trachea and/or main carina) can be automatically designated to be the linked structures, and any remaining discontinuous components are identified as isolated structures. Optionally, the operator can provide input identifying the isolated structures and/or the linked structures.

At step 120, the method 100 continues with outputting a graphical representation of the linked structures and at least one isolated structure. The graphical representation can be or include a 3D graphical representation, such as a 3D model of the anatomic region (e.g., the 3D model of step 110). Alternatively or in combination, the graphical representation can be or include a 2D graphical representation, such as one or more 2D images of the anatomic region. The 2D images can include actual images of the anatomy (e.g., CT images and/or other image data used to produce the 3D model of step 110). In some embodiments, the 2D images are part of a sequence of image data, with each 2D image representing a different image slice or section. Optionally, the 2D images can include virtual images of the anatomy (e.g., simulated 2D slices or sections of the 3D model). The 2D and/or 3D graphical representations can visually differentiate the isolated structures from the linked structures, e.g., based on color, transparency, texture, shading, labels, markings, and/or any other suitable visual indicator or element. Accordingly, an operator can view the graphical representation to determine the presence and/or locations of the isolated structures.

In some embodiments, the graphical representation is displayed as a part of a graphical user interface for assisting an operator in planning a medical procedure. The graphical user interface can be displayed on a suitable output device (e.g., monitor, touchscreen, etc.), and can allow the operator to provide instructions, commands, feedback, etc., via a suitable input device (e.g., mouse, keyboard, joystick, touchscreen, etc.). The graphical user interface can include functionality for viewing images and/or models of the patient anatomy, as well as for planning a path to a target site. The graphical user interface can also allow the operator to provide input to reconnect the isolated structures to the linked structures, as described further below.

Figure 3A:
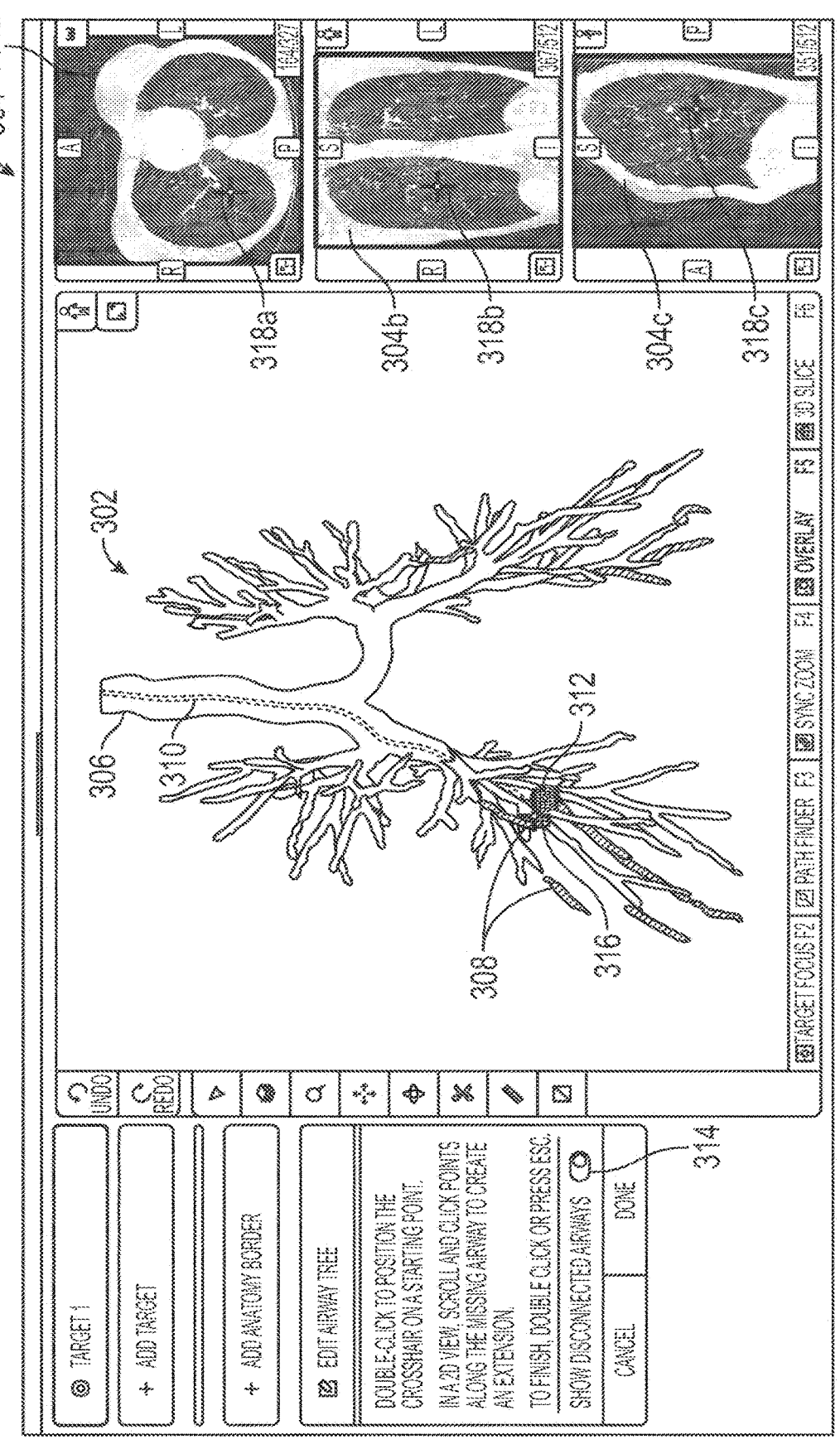
FIG. 3A illustrates a representative example of a graphical user interface configured in accordance with embodiments of the present technology.

FIG. 3A illustrates a representative example of a graphical user interface 300 ("interface 300") configured in accordance with embodiments of the present technology. The interface 300 includes a 3D model 302 of an anatomic region, and one or more 2D images 304 (three are shown as 2D images 304a-c) of the anatomic region. In the illustrated embodiment, the 3D model 302 and 2D images 304 are displayed separately from each other in a side-by-side configuration. In other embodiments, however, the 3D model 302 and 2D images 304 can be arranged differently in the interface 300.

The 3D model 302 can be identical or generally similar to the 3D model 200 of FIG. 2. For example, the 3D model 302 can include a set of linked structures 306 and one or more isolated structures 308, which can be visually distinguished from each other by color, transparency, shading, etc., as described above. The 3D model 302 can also include a path 310 to a target site 312 in the anatomic region. The interface 300 provides various tools for the operator to interact with the 3D model 302. For example, the interface 300 can allow the operator to control whether the isolated structures 308 are displayed or hidden, e.g., via a toggle element 314 and/or any other suitable interface element. The interface 300 can also allow the operator to pan, rotate, zoom in, zoom out, and/or otherwise manipulate the view of the 3D model 302. Accordingly, the operator can use the 3D model 302 to visualize the 3D spatial relationships between the various model components, e.g., the linked structures 306, isolated structures 308, path 310, and/or target site 312.

The 2D images 304 can show the anatomic region from one or more different views and/or planes, such as one or more cardinal views. In the illustrated embodiment, for example, the 2D images 304 include a first image 304a in an axial plane, a second image 304b in a coronal plane, and a third image 304c in a sagittal plane. In other embodiments, however, the interface 300 can include a different number of 2D images 304 (e.g., one, two, four, or more) and/or the 2D images 304 can depict different views of the anatomy. The interface 300 can include visual elements indicating ana-tomic directions so the operator can identify the displayed views (e.g., "L" for left, "R" for right, "S" for superior, "I" for inferior, "A" for anterior, "P" for posterior; icons rep-resenting the patient orientation; etc.). Additionally, the displayed views can alternatively or additionally include at least one view that is oblique (e.g., rotated) relative to a cardinal view. In embodiments where an oblique view is displayed, the interface 300 can overlay a plane representing the plane of the oblique view onto the 3D model 302. The interface 300 can allow the operator to pan, zoom in, zoom out, scroll through different image slices or sections, and/or otherwise manipulate the 2D images 304.

In some embodiments, the 2D images 304 are actual images of the patient anatomy, e.g., CT images obtained during a preoperative imaging procedure. Some or all of the 2D images 304 can be the same images used to generate the 3D model 302, as discussed above in step 110. When the operator selects a location in the 3D model 302, (e.g., as indicated by crosshairs 316), the interface 300 can automati-cally update the 2D images 304 to show the corresponding image slices depicting that location (e.g., as indicated by crosshairs 318a-c in images 304a-c, respectively). Con-versely, when the operator selects a location in one or more of the 2D images 304, the interface 300 can automatically update the location of the crosshairs 316 on the 3D model 302. Accordingly, the interface 300 can allow the operator to quickly and easily compare the 2D images 304 to the 3D model 302 to determine how the modeled structures corre-late to the actual anatomy. The interface 300 can also include other features to assist the operator in visualizing how the linked structures 306 and isolated structures 328 in the 3D model 302 correspond to the anatomy shown in the 2D images 304, as described in detail below with reference to FIGS. 3B and 3C.

Figure 3B:
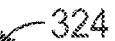
FIG. 3B illustrates a set of 2D images that can be displayed in the graphical user interface of FIG. 3A, in accordance with embodiments of the present technology.
Figure 3B:
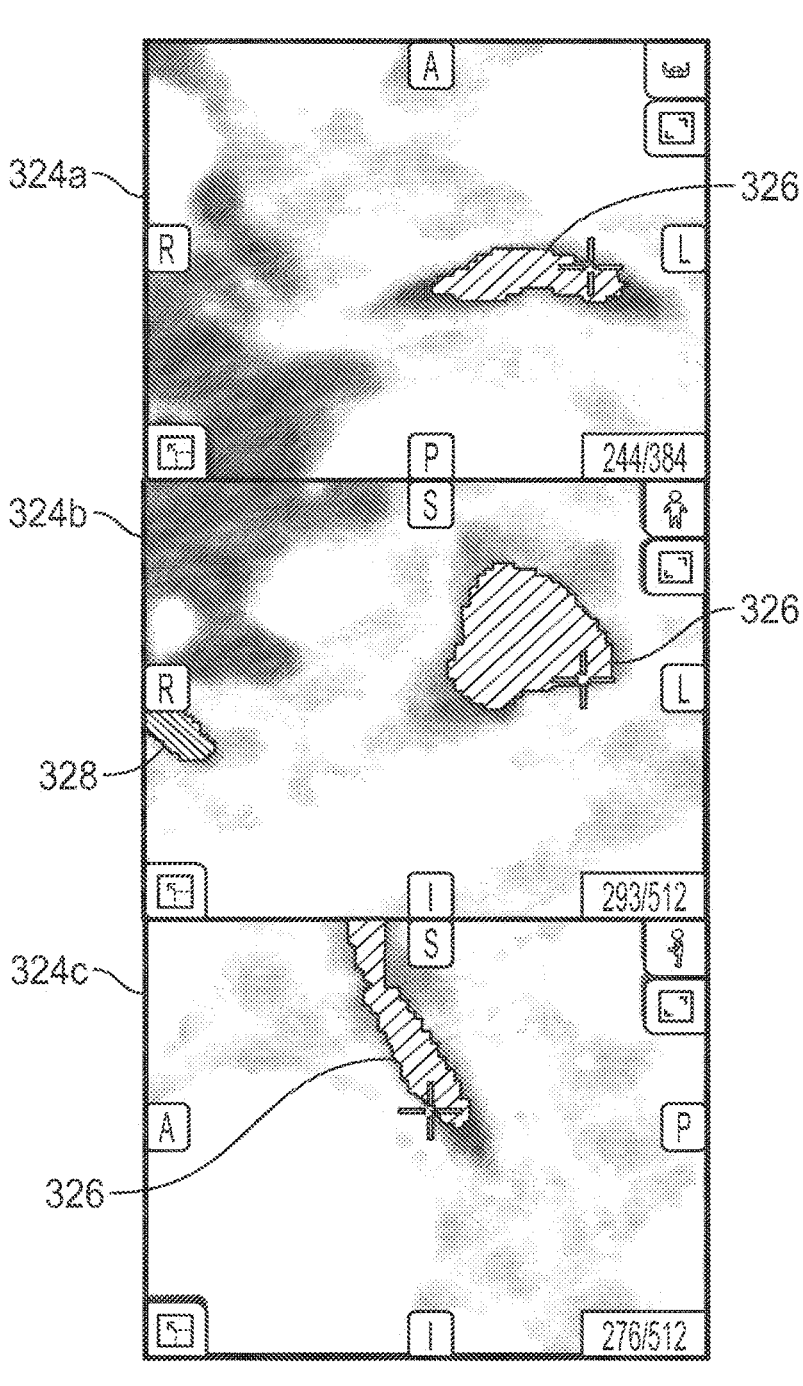

FIG. 3B illustrates a set of 2D images 324 (e.g., a first image 324a, a second image 324b, and a third image 324c) that can be displayed in the interface 300 of FIG. 3A, in accordance with embodiments of the present technology. The 2D images 324 can be generally similar to the 2D images 304 of FIG. 3A. As shown in FIG. 3B, the 2D images 324 include visual indicators (e.g., graphics, labels, markers, etc.) showing which portions correspond to the linked struc-tures 306 (FIG. 3A) and the isolated structures 308 (FIG.

3A) in the 3D model 302 (FIG. 3A). In the illustrated embodiment, for example, a set of first regions 326 is overlaid onto the 2D images 324 to represent the linked structures 306 (FIG. 3A), and a set of second regions 328 is overlaid onto the 2D images 324 to represent the isolated structures 308 (FIG. 3A). The first and second regions 326, 328 can be visually distinguished from each other using color, transparency, shading, texturing, etc. Accordingly, by comparing the 2D images 324 to the 3D model 302 (FIG. 3A), the operator can determine how the linked structures 306 and isolated structures 308 shown in the 3D model 302 correspond to the features of anatomic region. Optionally, the operator can use the 2D images 324 to determine whether the isolated structures 308 depicted in the 3D model 302 represent actual anatomic passageways (e.g., airways), or are non-anatomic structures or artifacts.

Figure 3C:
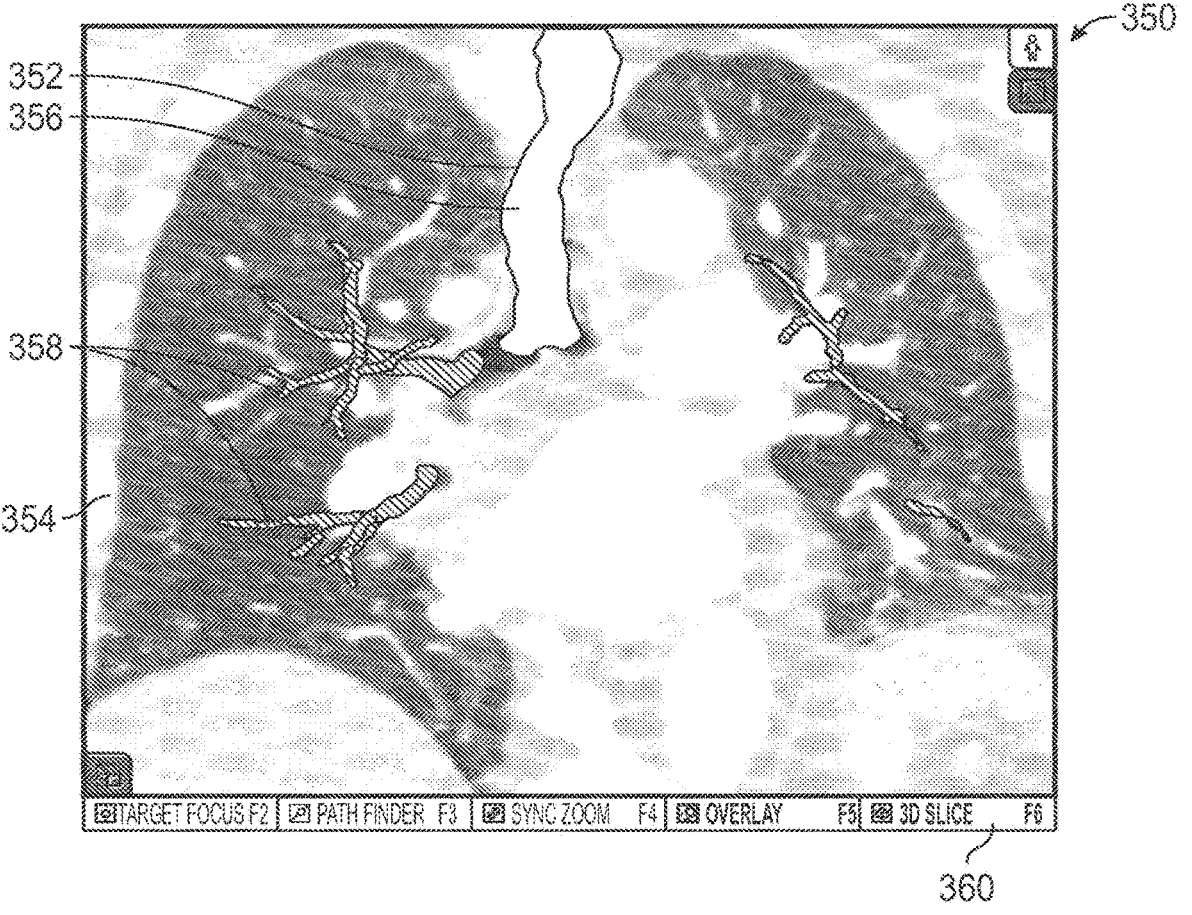
FIG. 3C illustrates an overlay view that can be displayed in the graphical user interface of FIG. 3A in accordance with embodiments of the present technology.

FIG. 3C illustrates an overlay view 350 that can be displayed in the interface 300, in accordance with embodi-ments of the present technology. The overlay view 350 can show a 3D model 352 and a 2D image 354 overlaid onto the 3D model 352. The 3D model 352 can be identical or generally similar to the 3D model 302 of FIG. 3A, and can depict a set of linked structures 356 and one or more isolated structures 358. The 2D image 354 can be identical or similar to any one of the 2D images 304 of FIG. 3A and/or the 2D images 324 of FIG. 3B. For example, the 2D image 354 can be a CT image showing a 2D slice of the patient anatomy. The 2D image 354 can be positioned and oriented relative to the 3D model 354 at the spatial plane corresponding to the plane of the 2D image 354, such that the features in the 2D image 354 are aligned with the corresponding components of the 3D model 352. Optionally, when the operator selects different locations in the 3D model 352 (e.g., by clicking, scrolling, etc.), the overlay view 350 can automatically update which 2D image 354 is displayed, as well as the location of the 2D image 354 relative to the 3D model 352. Accordingly, the operator can use the overlay view 350 to quickly and easily compare anatomical features depicted in the 2D image 354 to the structures in the 3D model 352. In some embodiments, the operator can switch between the overlay view 350 and the normal view of the 3D model 302 (FIG. 3A), such as by clicking on an interface element (e.g., button 360), entering a command, etc.

Referring again to FIG. 1, at step 130, the method 100 continues with receiving input indicating a set of locations representing a connection between the isolated structure and the linked structures. In some embodiments, the operator uses an input device (e.g., keyboard, mouse, joystick, touch-screen, etc.) to select one or more locations on the 2D and/or 3D graphical representations of the isolated structure and linked structures. For example, as previously described, the operator can view a graphical user interface (e.g., interface 300 of FIGS. 3A-3C) displaying the 3D model of the anatomic region and/or 2D images of the patient anatomy. The operator can provide input selecting one or more locations in the 3D model ("model locations"), one or more locations in the 2D images ("image locations"), or suitable combinations thereof. The selected locations can include points (e.g., 2D or 3D coordinate points), line segments, regions, volumes, etc., that partially or fully define a con-nection (also referred to as a "bridge" or "extension") between the isolated structure and the set of linked struc-tures.

The connection can be defined based on the operator input in many different ways. In some embodiments, for example, the operator selects a first location in or near the isolated structure (e.g., a tip or portion of the isolated structure closest to the linked structures), and a second location in or near the linked structures (e.g., a tip or portion of the linked structures closest to the isolated structure). The first and second locations can serve as the end points of the connection. The intermediate points of the connection can be determined automatically from the end points by a computing system (e.g., a system for planning the medical procedure, or any other suitable system or device). For example, the system can automatically generate a line (e.g., a straight or curved line) connecting the end points. Optionally, the operator can also define at least some of the intermediate points by selecting one or more intermediate locations between the first and second locations (e.g., locations in the gap between the isolated structure and the linked structures). Subsequently, the system can determine the connection by generating a plurality of line segments (e.g., linear or curved line segments) connecting the points defined by the operator. This approach can be helpful for defining for more complex connection geometries (e.g., nonlinear connections).

As another example, the operator can simply identify the structures to be connected, and the system can automatically determine the connection between the identified structures. For example, the operator can identify the isolated structure by selecting one or more locations in or near the isolated structure, and can identify the linked structures by selecting one or more locations in or near the linked structures. The system can analyze the spatial arrangement and/or geometries of the isolated and linked structures to determine how the structures should be connected. For example, the system can identify the portions of the isolated and linked structures that are closest to each other, and can generate a connection (e.g., a straight or curved line) between the identified portions. The system can display the generated connection so the operator can review, and, if appropriate, approve, reject, or modify the connection.

Optionally, the system can consider anatomic information when generating the connection between the isolated and linked structures, in addition to the operator input described above. For example, the system can analyze image data of the anatomic region (e.g., CT images) to identify the probable locations of anatomic passageways between the isolated and linked structures. Subsequently, the system can constrain the connection to overlap or be within a predetermined distance of the identified locations. Alternatively, the system may not constrain the connection, but may alert to the operator if the connection is not sufficiently close to or lies outside the identified locations.

Figure 4A:
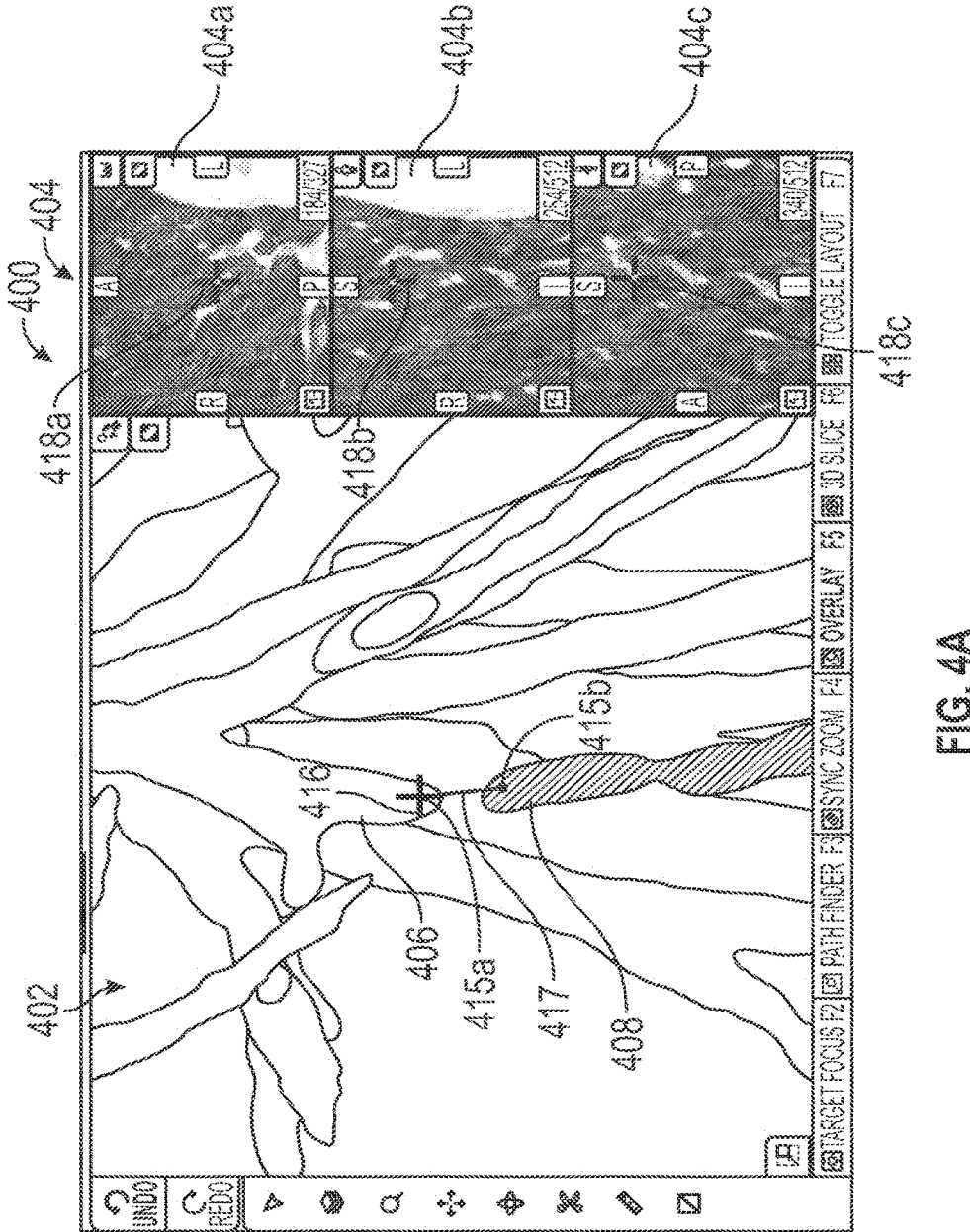
FIGS. 4A-4C illustrate a representative example of a graphical user interface with various modes for defining a connection between isolated and linked structures in accordance with embodiments of the present technology.
Figure 4B:
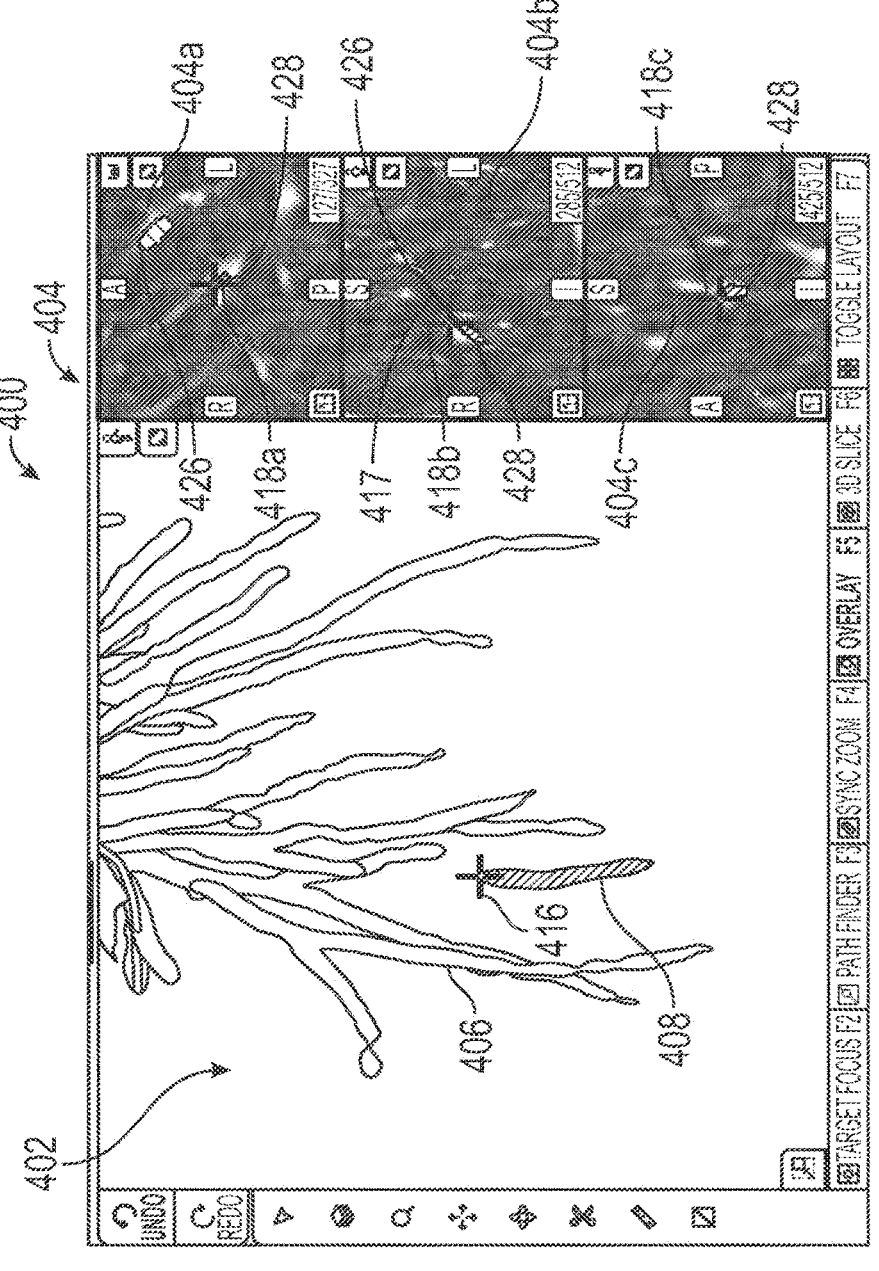
Figure 4C:
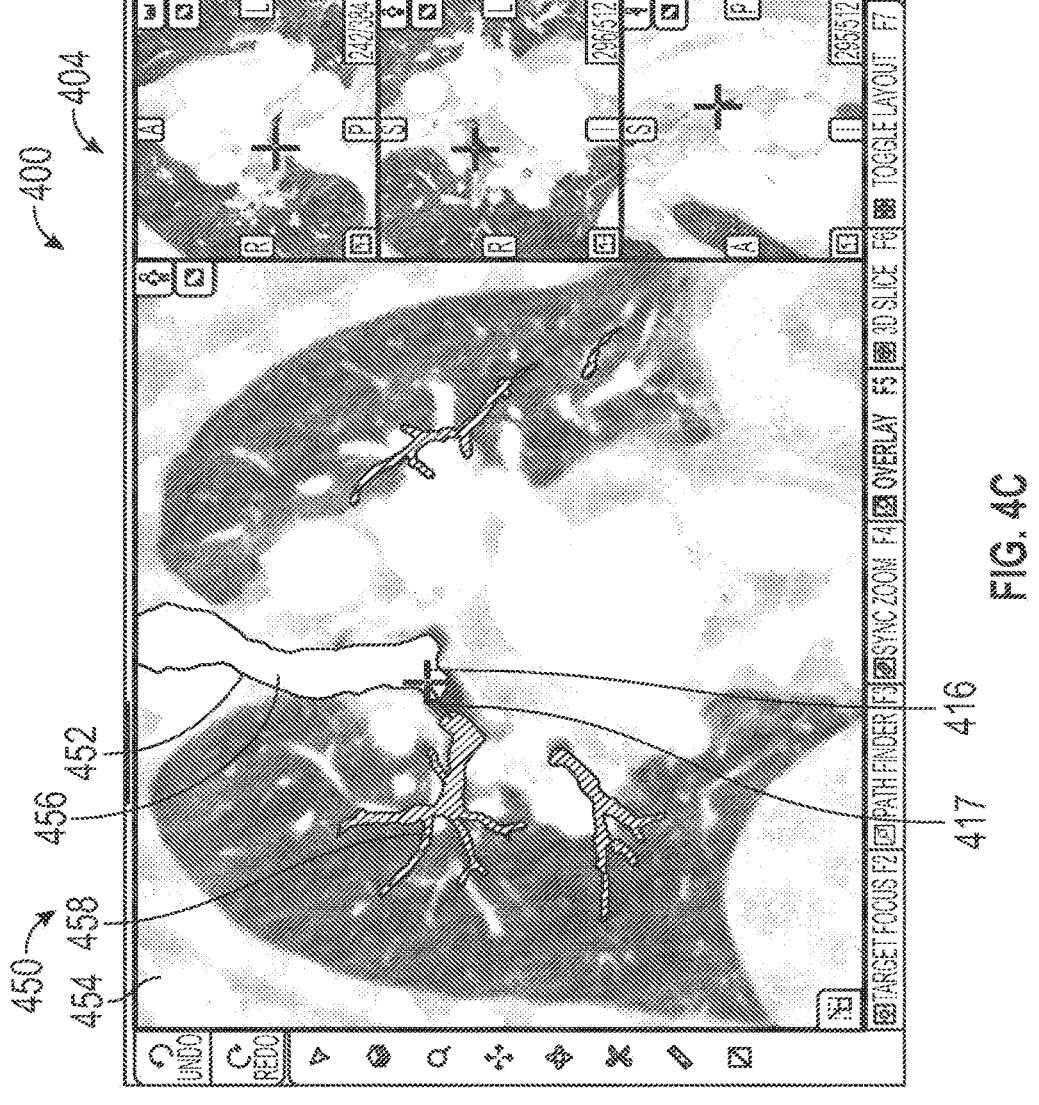

FIGS. 4A-4C illustrate a representative example of a graphical user interface 400 ("interface 400") with various modes for defining a connection between isolated and linked structures, in accordance with embodiments of the present technology. In particular, FIG. 4A illustrates the interface 400 during a 3D connection mode, FIG. 4B illustrates the interface 400 during a 2D connection mode, and FIG. 4C illustrates the interface 400 during a hybrid connection mode. The interface 400 can be identical or generally similar to the interface 300 of FIGS. 3A-3C, such that like numbers are used to identify similar or identical components (e.g., 3D model 402 versus 3D model 302). Additionally, any of the features described in FIGS. 4A-4C can be combined with any of the features of the interface 300 of FIGS. 3A-3C, and vice-versa.

Referring first to FIG. 4A, the interface 400 includes a 3D model 402 having a set of linked structures 406 and at least one isolated structure 408, and one or more 2D images 404 (three are shown as 2D images 404a-c). When using a 3D connection mode, the operator can define a connection between the linked structures 406 and the isolated structure 408 by selecting a set of model locations in the 3D model 402. Each model location can be represented as a set of 3D coordinates in the reference frame of the 3D model 402. As shown in FIG. 4A, for example, the operator can select a first model location 415a (e.g., a location in the linked structures 406) in the 3D model 402. The interface 400 can display a first visual indicator (e.g., crosshairs 416) at the first model location 415a. The operator can then select a second model location 415b (e.g., a location in the isolated structure 408) in the 3D model 402. Optionally, the interface 400 can display a second visual indicator (not shown) at the second model location 415b. If desired, the operator can continue with selecting additional model locations, as described above. The model locations 415a-b can be used to determine a connection between the linked structures 406 and isolated structure 408, as previously discussed. The interface 400 can optionally display a third visual indicator (e.g., line segment 417) overlaid on the 3D model 402 to represent the connection.

In some embodiments, the interface 400 also displays one or more visual indicators on the 2D images 404 to represent the image locations corresponding to the model locations 415a-b. Each image location can be represented as a set of 3D coordinates in the reference frame of the 2D images 404 (e.g., the X and Y coordinates correspond to the location in the plane of an individual 2D image 404, and the Z coordinate corresponds to the position of that 2D image 404 in the image stack). In embodiments where the 2D images 404 are used to generate the 3D model 402, the mapping between the model and image reference frames is already known (e.g., the model and image reference frames can be the same reference frame). Accordingly, the model locations can be easily mapped to image locations, and vice-versa.

In the illustrated embodiment, for example, the interface 400 includes crosshairs 418a-c overlaid on each of the 2D images 404a-c, respectively, at the image locations corresponding to the first model location 415a. Optionally, as the operator selects additional model locations (e.g., the second model location 415b), the interface 400 can determine and/or show additional image locations. As previously described, the interface 400 can automatically update the displayed 2D images 404 to show the appropriate image slices (e.g., the image slices with the image locations corresponding to the most recently selected model location). Accordingly, the operator can view the 2D images 404 to verify whether the model locations 415a-b and/or generated connection accurately represent the actual anatomic connection. Optionally, the interface 400 can output a prompt or other notification reminding the operator to also review the 2D images 404 when defining a connection via the 3D model 402.

Referring next to FIG. 4B, when using a 2D connection mode, the operator can define the connection between the linked structures 406 and the isolated structure 408 by selecting a set of image locations in the 2D images 404. The 2D connection mode may improve accuracy in some situations because the operator defines the connection by directly selecting locations in the images of the actual anatomy. To facilitate the selection process, the interface 400 can include colored regions 426, 428 overlaid on the 2D images 404 to show the locations of the linked structures 406 and the isolated structure 408, respectively. The operator can select a first image location in or near the linked structures 406, and a second image location in or near the isolated structure 408. Optionally, the operator can select one or more additional image locations between the linked structures 406 and the isolated structure 408. In embodiments where some or all of the image locations are in different image slices (e.g., different coronal, axial, and/or sagittal slices), the operator can use the interface 400 to navigate (e.g., scroll) through the image slices to view and select the desired image locations. The interface 400 can display visual indicators on the 2D images 404 (e.g., crosshairs 418*a-c*) to represent some or all of the selected image locations.

The selected image locations can be used to define a connection between the linked structures 406 and the isolated structures 408 in the 3D model 402. For example, the selected image locations can be used to determine a corresponding set of model locations (e.g., end points and/or intermediate points). As described above, each image location can be represented as a set of 3D coordinates in the reference frame of the 2D images 404, and the mapping between the image and model coordinates can be known (e.g., the 3D model 402 and 2D images 404 can be the same reference frame). Accordingly, the image locations can be mapped to corresponding model locations, and the model locations can be used to generate the connection (e.g., by bridging the end points and/or intermediate points with line segments), as previously described. The interface 400 can output a visual indicator on one or more of the 2D images 408 (e.g., line segment 419 on the second image 404*b*) to represent the generated connection. Optionally, the interface 400 can also display visual indicators on the 3D model 402 (e.g., crosshairs 416) to represent the model locations and/or connection, as previously described with reference to FIG. 4A.

Referring next to FIG. 4C, when using a hybrid connection mode, the operator can select locations using an overlay view 450 that shows a 2D image 454 overlaid onto a 3D model 452. As previously described with reference to FIG. 3C, the overlay view 450 can make it easier for the operator to see how the locations of the linked structures 456 and isolated structure 458 correlate to the patient anatomy depicted in the 2D image 454. The operator can select a set of model locations in the 3D model 452 to define the connection between the isolated structure 458 and the linked structures 456. The process of selecting model locations and generating a connection can be identical or generally similar to the processes described above with reference to FIG. 4A. Similarly, the interface 400 can output various visual indicators on the 3D model 452, the overlaid 2D image 454, and/or the other 2D images 404 to show the selected model location(s) and/or the generated connection. In the illustrated embodiment, for example, the interface 400 includes a set of crosshairs 416 on the 3D model 452 representing a first model location, and a line segment 417 representing the connection between the linked structures 452 and the isolated structure 458.

Referring again to FIG. 1, at step 140, the method 100 includes generating a bridge structure connecting the isolated structure to the linked structures. The bridge structure can be a 3D shape, volume, etc., representing an anatomic passageway between the isolated structure and the linked structures. The bridge structure can be generated based on the operator input received in step 130. For example, the operator input can define a connection between the isolated structure and the linked structures, as previously discussed, and the connection can be used to determine a set of seed points for growing the bridge structure (e.g., some or all of the points along the connection can be used as the seed points). In some embodiments, the seed points are input into a growing algorithm (e.g., a region or volume growing algorithm), along with image data of the anatomic region (e.g., the 2D images used to generate the 3D model). The seed points can define an initial region or volume for the algorithm. The algorithm can analyze the graphical units (e.g., pixels or voxels) adjacent or near the seed points to determine whether they should be added to the region or volume (e.g., based on similarity in color, brightness, etc.). This process can be repeated to iteratively grow the bridge structure from the seed points. Optionally, the algorithm can weight different seed points differently during the growing process. For example, points that were selected by the operator (e.g., the locations selected in step 130) can be weighted more heavily than points that were generated automatically. As another example, points that are determined to be lying outside anatomic passageways (e.g., based on the image data) can be weighted less heavily or discarded altogether. In other embodiments, however, other algorithms or techniques for growing, segmenting, or otherwise generating the bridge structure from the seed points can be used.

At step 150, the method 100 can include outputting a graphical representation of the bridge structure. The graphical representation can be a 3D graphical representation (e.g., a component of the 3D model of the anatomic region), a 2D graphical representation (e.g., an overlay on the 2D images of the anatomic region), or a suitable combination thereof. The 2D and/or 3D graphical representations can visually distinguish the bridge structure from the other structures, such as via color, transparency, texture, shading, labels, markings, and/or any other suitable visual indicator. Accordingly, an operator can view the graphical representation to evaluate the location and/or geometry of the generated bridge structure, and, if appropriate, provide input to approve, reject, or modify the bridge structure. The graphical representation can be displayed as part of a graphical user interface (e.g., the interface 300 of FIGS. 3A-3C and/or the interface 400 of FIGS. 4A-4C).

Figure 5:
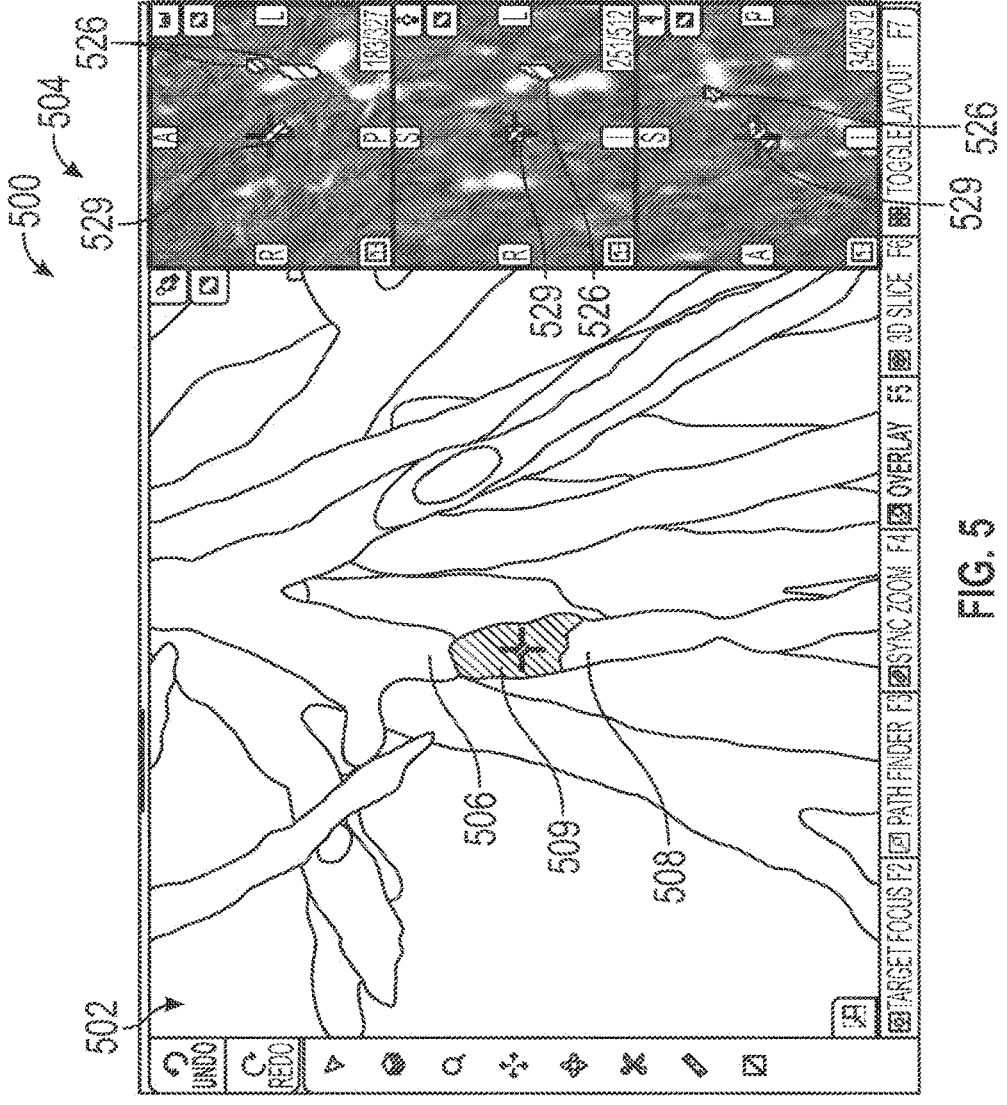
FIG. 5 illustrates a representative example of a graphical user interface for displaying a bridge structure in accordance with embodiments of the present technology.

FIG. 5 illustrates a representative example of a graphical user interface 500 ("interface 500") for displaying a bridge structure in accordance with embodiments of the present technology. The interface 500 can be identical or generally similar to the interface 300 of FIGS. 3A-3C and/or the interface 400 of FIGS. 4A-4C, such that like numbers are used to identify similar or identical components (e.g., 3D model 502 versus 3D model 302). Additionally, any of the features described in FIG. 5 can be combined with any of the features of the interface 300 of FIGS. 3A-3C and/or the interface 400 of FIGS. 4A-4C, and vice-versa.

The interface 500 includes a 3D model 502 and a set of 2D images 504 depicting an anatomic region. As shown in FIG. 5, the 3D model 502 includes a bridge structure 509 connecting a set of linked structures 506 to a previously isolated structure 508. The bridge structure 509 can be visually differentiated from the linked structures 506 and/or the isolated structure 508 using different colors, transparency, shading, etc. (indicated by hatching in FIG. 5). The interface 500 can also include a set of colored regions 529 overlaid onto the 2D images 504 to represent the bridge structure 509, so the operator can visualize how the bridge structure 509 correlates to the imaged anatomy. The regions 529 can also be visually distinguished from additional colored regions 526 representing other portions of the model 502 (e.g., the linked structures 506 and/or the isolated structure 508), e.g., using color and/or other suitable indicators. Optionally, the interface 500 alternatively or additionally show the bridge structure 509 in an overlay view (not shown), which can be identical or generally similar to the overlay view 350 of FIG. 3C and/or the overlay view 450 of FIG. 4C.

Referring again to FIG. 1, although the steps of the method 100 are discussed and illustrated in a particular order, a person of ordinary skill in the relevant art will recognize that the method 100 can be altered and still remain within these and other embodiments of the present technology. In other embodiments, for example, the method 100 can be performed in a different order, e.g., any of the steps of the method 100 can be performed before, during, and/or after any of the other steps of the method 100. Additionally, one or more steps of the method 100 illustrated in FIG. 1 can be omitted. Optionally, one or more steps of the method 100 can be repeated. For example, in embodiments where the 3D model includes multiple isolated structures (e.g., two, three, four, five, ten, or more isolated structures), steps 120-150 can be performed multiple times to connect each isolated structure to the rest of the model.

B. EMBODIMENTS OF ROBOTIC OR TELEOPERATED MEDICAL SYSTEMS AND ASSOCIATED DEVICES, SYSTEMS, AND METHODS

Figure 6:
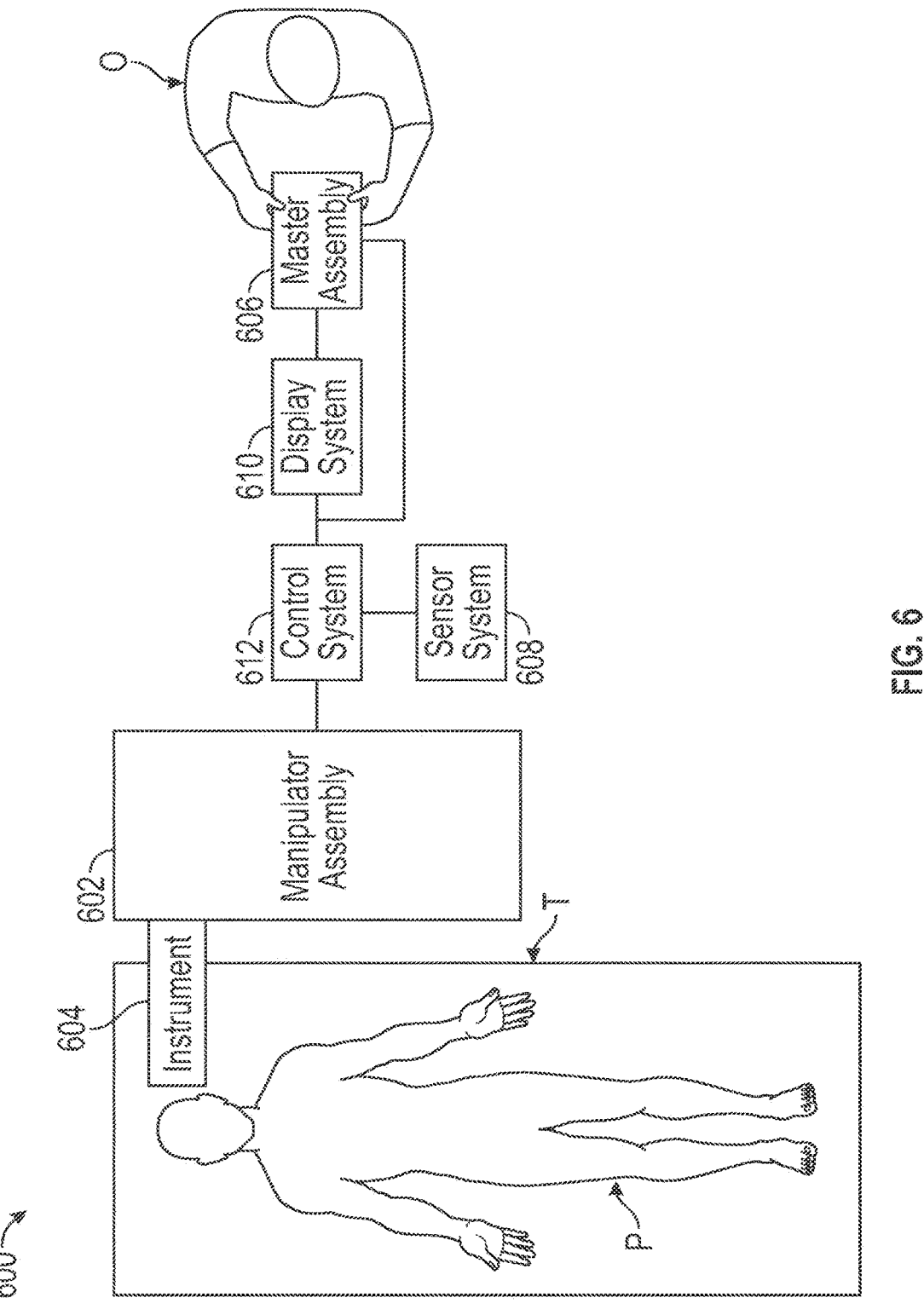
FIG. 6 is a simplified diagram of a teleoperated medical system configured in accordance with various embodiments of the present technology.

FIG. 6 is a schematic representation of a robotic or teleoperated medical system 600 ("medical system 600") configured in accordance with various embodiments of the present technology. The medical system 600 can be used with any of the procedures or methods described above with respect to FIGS. 1-5. For example, an operator can use the medical system 600 to review a 3D model of an anatomic region and reconnect one or more isolated structures in the model, as previously described. The 3D model can be used to plan and/or perform a medical procedure using the medical system 600.

In some embodiments, the medical system 600 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 6, the medical system 600 generally includes a manipulator assembly 602 for operating a medical instrument 604 in performing various procedures on a patient P positioned on a table T. The manipulator assembly 602 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated.

The medical system 600 further includes a master assembly 606 having one or more control devices for controlling the manipulator assembly 602. The manipulator assembly 602 supports the medical instrument 604 and may optionally include a plurality of actuators or motors that drive inputs on the medical instrument 604 in response to commands from a control system 612. The actuators may optionally include drive systems that, when coupled to the medical instrument 604, may advance the medical instrument 604 into a naturally or surgically created anatomic orifice. Other drive systems may move the distal end of the medical instrument 604 in multiple degrees of freedom, which may include three degrees of linear motion (e.g., linear motion along the X, Y, and Z Cartesian axes) and in three degrees of rotational motion (e.g., rotation about the X, Y, and Z Cartesian axes). Additionally, the actuators can be used to actuate an articulable end effector of the medical instrument 604 for grasping tissue in the jaws of a biopsy device and/or the like. Actuator position sensors such as resolvers, encoders, potentiometers, and other mechanisms may provide sensor data to the medical system 600 describing the rotation and orientation of the motor shafts. This position sensor data may be used to determine motion of the objects manipulated by the actuators.

The medical system 600 also includes a display system 610 for displaying an image or representation of the surgical site and the medical instrument 604 generated by subsystems of a sensor system 608. For example, the display system 610 can display a 3D anatomic model generated in accordance with the techniques described herein. Optionally, the display system 610 can display auxiliary information related to a procedure, such as information related to ablation (e.g., temperature, impedance, energy delivery power levels, frequency, current, energy delivery duration, indicators of tissue ablation, etc.). The display system 610 and the master assembly 606 may be oriented so an operator O can control the medical instrument 604 and the master assembly 606 with the perception of telepresence.

In some embodiments, the medical instrument 604 may include components of an imaging system, which may include an imaging scope assembly or imaging instrument that records a concurrent or real-time image of a surgical site and provides the image to the operator O through one or more displays of the medical system 600, such as one or more displays of the display system 610. The concurrent image may be, for example, a 2D or 3D image captured by an imaging instrument positioned within the surgical site. In some embodiments, the imaging system includes endoscopic imaging instrument components that may be integrally or removably coupled to the medical instrument 604. In some embodiments, however, a separate endoscope, attached to a separate manipulator assembly may be used with the medical instrument 604 to image the surgical site. In some embodiments, the imaging system includes a channel (not shown) that may provide for delivery of instruments, devices, catheters, etc., as described herein. The imaging system may be implemented as hardware, firmware, software, or a combination thereof which interact with or are otherwise executed by one or more computer processors, which may include the processors of the control system 612.

The medical system 600 may also include the control system 612. The control system 612 includes at least one memory and at least one computer processor (not shown) for effecting control the between medical instrument 604, the master assembly 606, the sensor system 608, and the display system 610. The control system 612 also includes programmed instructions (e.g., a non-transitory machine-readable medium storing the instructions) to implement some or all of the methods described in accordance with aspects disclosed herein, including instructions for providing information to the display system 610.

The control system 612 may optionally further include a virtual visualization system to provide navigation assistance to the operator O when controlling the medical instrument 604 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as CT, MRI, fluoroscopy, thermography, ultrasound, OCT, thermal imaging, impedance imaging, laser imaging, nanotube X-ray imaging, and/or the like.

Figures 7A, 7B:
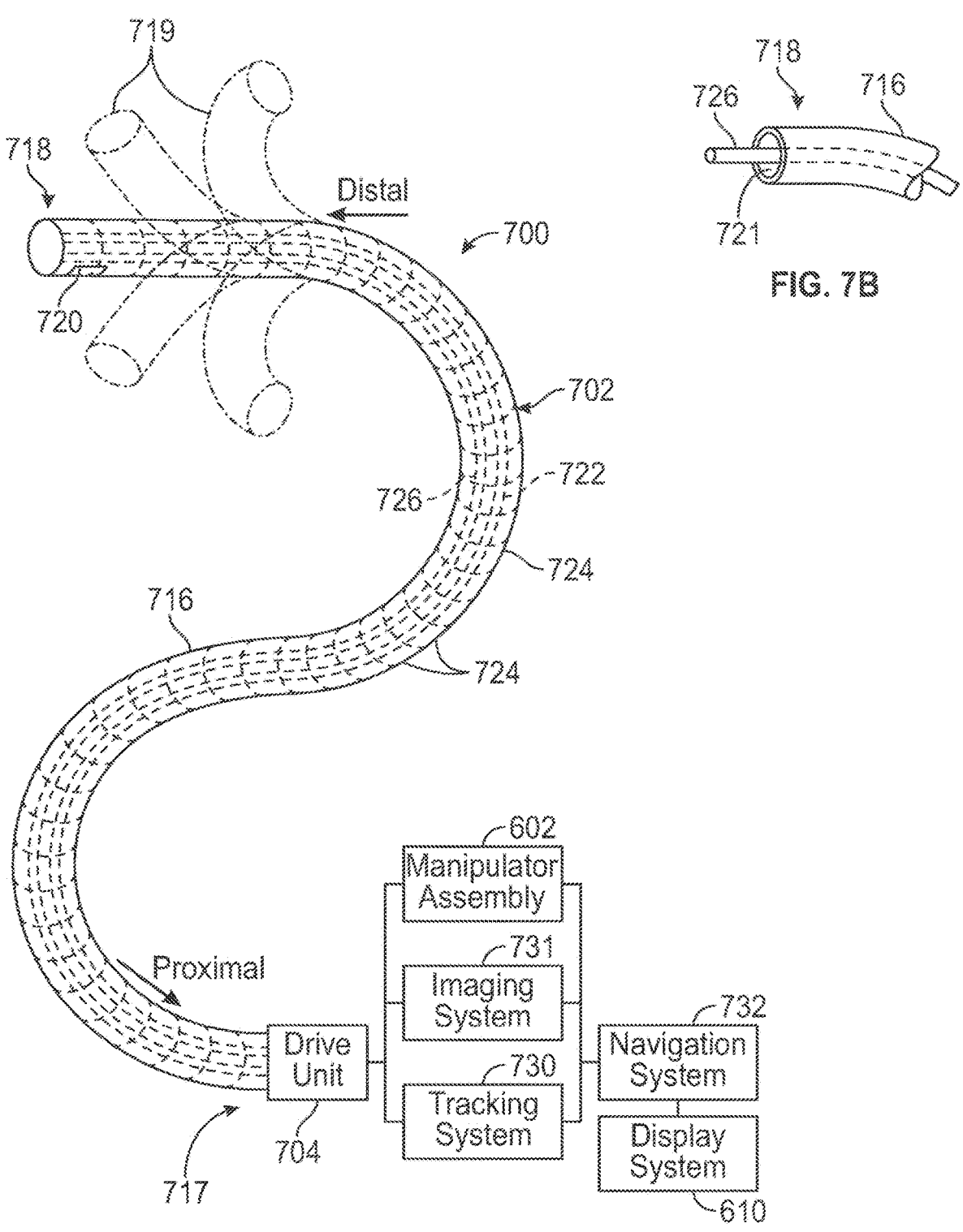
FIG. 7A is a simplified diagram of a medical instrument system configured in accordance with various embodiments of the present technology.
FIG. 7B is a simplified diagram of a medical instrument system configured in accordance with various embodiments of the present technology.

FIG. 7A is a simplified diagram of a medical instrument system 700 configured in accordance with various embodiments of the present technology. The medical instrument system 700 includes an elongate flexible device 702, such as a flexible catheter, coupled to a drive unit 704. The elongate flexible device 702 includes a flexible body 716 having a proximal end 717 and a distal end or tip portion 718. The medical instrument system 700 further includes a tracking system 730 for determining the position, orientation, speed, velocity, pose, and/or shape of the distal end 718 and/or of one or more segments 724 along the flexible body 716 using one or more sensors and/or imaging devices as described in further detail below.

The tracking system 730 may optionally track the distal end 718 and/or one or more of the segments 724 using a shape sensor 722. The shape sensor 722 may optionally include an optical fiber aligned with the flexible body 716 (e.g., provided within an interior channel (not shown) or mounted externally). The optical fiber of the shape sensor 722 forms a fiber optic bend sensor for determining the shape of the flexible body 716. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. Pat. No. 7,781,724, filed Sep. 26, 2006, disclosing "Fiber Optic Position and Shape Sensing Device and Method Relating Thereto"; U.S. Pat. No. 7,772,541, filed Mar. 12, 2008, disclosing "Fiber Optic Position and/or Shape Sensing Based on Rayleigh Scatter"; and U.S. Pat. No. 6,389,187, filed Apr. 21, 2000, disclosing "Optical Fiber Bend Sensor," which are all incorporated by reference herein in their entireties. In some embodiments, the tracking system 730 may optionally and/or additionally track the distal end 718 using a position sensor system 720. The position sensor system 720 may be a component of an electromagnetic (EM) sensor system with the position sensor system 720 including one or more conductive coils that may be subjected to an externally generated electromagnetic field. In some embodiments, the position sensor system 720 may be configured and positioned to measure six degrees of freedom (e.g., three position coordinates X, Y, and Z and three orientation angles indicating pitch, yaw, and roll of a base point) or five degrees of freedom (e.g., three position coordinates X, Y, and Z and two orientation angles indicating pitch and yaw of a base point). Further description of a position sensor system is provided in U.S. Pat. No. 6,380,732, filed Aug. 9, 1999, disclosing "Six-Degree of Freedom Tracking System Having a Passive Transponder on the Object Being Tracked," which is incorporated by reference herein in its entirety. In some embodiments, an optical fiber sensor may be used to measure temperature or force. In some embodiments, a temperature sensor, a force sensor, an impedance sensor, or other types of sensors may be included within the flexible body. In various embodiments, one or more position sensors (e.g. fiber shape sensors, EM sensors, and/or the like) may be integrated within the medical instrument 726 and used to track the position, orientation, speed, velocity, pose, and/or shape of a distal end or portion of medical instrument 726 using the tracking system 730.

The flexible body 716 includes a channel 721 sized and shaped to receive a medical instrument 726. FIG. 7B, for example, is a simplified diagram of the flexible body 716 with the medical instrument 726 extended according to some embodiments. In some embodiments, the medical instrument 726 may be used for procedures such as imaging, visualization, surgery, biopsy, ablation, illumination, irrigation, and/or suction. The medical instrument 726 can be deployed through the channel 721 of the flexible body 716 and used at a target location within the anatomy. The medical instrument 726 may include, for example, energy delivery instruments (e.g., an ablation probe), image capture probes, biopsy instruments, laser ablation fibers, and/or other surgical, diagnostic, or therapeutic tools. The medical instrument 726 may be used with an imaging instrument (e.g., an image capture probe) within the flexible body 716. The imaging instrument may include a cable coupled to the camera for transmitting the captured image data. In some embodiments, the imaging instrument may be a fiber-optic bundle, such as a fiberscope, that couples to an image processing system 731. The imaging instrument may be single or multi-spectral, for example capturing image data in one or more of the visible, infrared, and/or ultraviolet spectrums. The medical instrument 726 may be advanced from the opening of channel 721 to perform the procedure and then be retracted back into the channel 721 when the procedure is complete. The medical instrument 726 may be removed from the proximal end 717 of the flexible body 716 or from another optional instrument port (not shown) along the flexible body 716.

The flexible body 716 may also house cables, linkages, or other steering controls (not shown) that extend between the drive unit 704 and the distal end 718 to controllably bend the distal end 718 as shown, for example, by broken dashed line depictions 719 of the distal end 718. In some embodiments, at least four cables are used to provide independent "up-down" steering to control a pitch of the distal end 718 and "left-right" steering to control a yaw of the distal end 718. Steerable elongate flexible devices are described in detail in U.S. Pat. No. 9,452,276, filed Oct. 14, 2011, disclosing "Catheter with Removable Vision Probe," and which is incorporated by reference herein in its entirety. In various embodiments, medical instrument 726 may be coupled to drive unit 704 or a separate second drive unit (not shown) and be controllably or robotically bendable using steering controls.

The information from the tracking system 730 may be sent to a navigation system 732 where it is combined with information from the image processing system 731 and/or the preoperatively obtained models to provide the operator with real-time position information. In some embodiments, the real-time position information may be displayed on the display system 610 of FIG. 6 for use in the control of the medical instrument system 700. In some embodiments, the control system 612 of FIG. 6 may utilize the position information as feedback for positioning the medical instrument system 700. Various systems for using fiber optic sensors to register and display a surgical instrument with surgical images are provided in U.S. Pat. No. 8,900,131, filed May 13, 2011, disclosing "Medical System Providing Dynamic Registration of a Model of an Anatomic Structure for Image-Guided Surgery," which is incorporated by reference herein in its entirety.

In some embodiments, the medical instrument system 700 may be teleoperated within the medical system 600 of FIG. 6. In some embodiments, the manipulator assembly 602 of FIG. 6 may be replaced by direct operator control. In some embodiments, the direct operator control may include various handles and operator interfaces for hand-held operation of the instrument.

C. CONCLUSION

The systems and methods described herein can be provided in the form of tangible and non-transitory machine-readable medium or media (such as a hard disk drive, hardware memory, optical medium, semiconductor medium, magnetic medium, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. Programmed instructions may be implemented as a number of separate programs or subroutines, or they may be integrated into a number of other aspects of the systems described herein. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. In one embodiment, the control system supports wireless communication protocols such as Bluetooth, IrDA, HomeRF, IEEE 802.11, DECT, and Wireless Telemetry. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

Medical tools that may be delivered through the elongate flexible devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electro-surgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between their proximal and distal ends to controllably bend the distal ends of the tools. Steerable instruments are described in detail in U.S. Pat. No. 7,316, 681, filed Oct. 4, 2005, disclosing "Articulated Surgical Instrument for Performing Minimally Invasive Surgery with Enhanced Dexterity and Sensitivity" and U.S. Pat. No. 9,259,274, filed Sep. 30, 2008, disclosing "Passive Preload and Capstan Drive for Surgical Instruments," which are incorporated by reference herein in their entireties.

The systems described herein may be suited for navigation and treatment of anatomic tissues, via natural or surgically created connected passageways, in any of a variety of anatomic systems, including the lung, colon, stomach, intestines, kidneys and kidney calices, bladder, liver, gall bladder, pancreas, spleen, ureter, ovaries, uterus, brain, the circulatory system including the heart, vasculature, and/or the like.

Although many of the embodiments are described above in the context of navigating and performing medical procedures within lungs of a patient, other applications and other embodiments in addition to those described herein are within the scope of the present technology. For example, unless otherwise specified or made clear from context, the devices, systems, methods, and computer program products of the present technology can be used for various image-guided medical procedures, such as medical procedures performed on, in, or adjacent hollow patient anatomy, and, more specifically, in procedures for surveying, biopsying, ablating, or otherwise treating tissue within and/or proximal the hollow patient anatomy. Thus, for example, the systems, devices, methods, and computer program products of the present disclosure can be used in one or more medical procedures associated with other patient anatomy, such as the bladder, urinary tract, GI system, and/or heart of a patient.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian X, Y, and Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

As used herein, the term "operator" shall be understood to include any type of personnel who may be performing or assisting a medical procedure and, thus, is inclusive of a physician, a surgeon, a doctor, a nurse, a medical technician, other personnel or user of the technology disclosed herein, and any combination thereof. Additionally, or alternatively, the term "patient" should be considered to include human and/or non-human (e.g., animal) patients upon which a medical procedure is being performed.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A system for planning a medical procedure, the system comprising:
   a processor; and
   a memory operably coupled to the processor and storing instructions that, when executed by the processor, cause the system to perform operations comprising:
      receiving a three-dimensional (3D) model of an anatomic region of a patient, wherein the 3D model includes a set of linked structures and at least one isolated structure spaced apart from the linked structures;
      outputting a graphical representation of the linked structures and the at least one isolated structure;
      receiving operator input indicating a set of locations on the graphical representation, the set of locations representing a connection between the at least one isolated structure and the linked structures, wherein at least one location of the set of locations identifies at least one linked structure of the set of linked structures; and
      generating, based on the operator input, a bridge structure connecting the at least one isolated structure to the linked structures.

2. The system of claim 1 wherein the graphical representation includes the 3D model.

3. The system of claim 2 wherein the set of locations includes a first model location and a second model location in the 3D model.

4. The system of claim 3 wherein the first model location is within or near the at least one isolated structure, and the second model location is within or near at least one of the linked structures.

5. The system of claim 3 wherein the operations further comprise determining one or more intermediate model locations between the first and second model locations.

6. The system of claim 5 wherein the one or more intermediate model locations are along a linear or curved connection between the first and second model locations.

7. The system of claim 5 wherein the operations further comprise inputting the first model location, the second model location, and the one or more intermediate model locations into a segmentation algorithm.

8. The system of claim 1 wherein the graphical representation includes one or more two-dimensional (2D) images of the anatomic region.

9. The system of claim 8 wherein the set of locations includes a first image location and a second image location in the one or more 2D images.

10. The system of claim 9 wherein the first image location corresponds to the at least one isolated structure, and the second image location corresponds to at least one of the linked structures.

11. The system of claim 9 wherein the first and second image locations are in different 2D images of the anatomic region.

12. The system of claim 9 wherein the operations further comprise mapping the first and second image locations to corresponding first and second model locations in the 3D model.

13. The system of claim 1 wherein the graphical representation includes the 3D model and one or more 2D images of the anatomic region.

14. The system of claim 13 wherein the graphical representation includes at least one 2D image overlaid on the 3D model.

15. The system of claim 1 wherein the operations further comprise receiving image data of the anatomic region, and wherein the bridge structure is generated based, at least in part, on the image data.

16. The system of claim 15 wherein generating the bridge structure includes segmenting the image data using a segmentation algorithm, and wherein at least some of the set of locations are used as seed points for the segmentation algorithm.

17. The system of claim 1 wherein the operations further comprise:

receiving operator input confirming the at least one isolated structure is an anatomic structure.

18. A non-transitory, computer-readable medium storing instructions thereon that, when executed by one or more processors of a computing system, cause the computing system to perform operations comprising:

outputting a graphical user interface including:

a three-dimensional (3D) model of an anatomic region of a patient, wherein the 3D model includes a set of linked structures and at least one isolated structure spaced apart from the linked structures, and a plurality of two-dimensional (2D) images of the anatomic region of the patient;

receiving, via the graphical user interface, operator input indicating a set of locations in one or more of the 3D model or the 2D images, the set of locations representing a connection between the at least one isolated structure and the linked structures, wherein at least one location of the set of locations identifies at least one linked structure of the set of linked structures; and updating the 3D model, based on the operator input, to include a bridge structure connecting the at least one isolated structure to the linked structures.

19. The non-transitory, computer-readable medium of claim 18 wherein the graphical user interface displays the at least one isolated structure together with the linked structures, and the at least one isolated structure is visually distinguished from the linked structures.

20. The non-transitory, computer-readable medium of claim 19 wherein the graphical user interface visually distinguishes the at least one isolated structure from the linked structures using one or more of coloring, shading, transparency, or texture.

* * * * *